(12) United States Patent
Kudoh

(10) Patent No.: US 8,955,470 B2
(45) Date of Patent: Feb. 17, 2015

(54) GAS-LIQUID MIXING NOZZLE, AND EMULSION FUEL COMBUSTION SYSTEM AND ENVIRONMENT PURIFICATION LIQUID SPRAY SYSTEM THAT USE THE SAME

(75) Inventor: Yasushi Kudoh, Tokyo (JP)

(73) Assignee: Lead Industry Company Ltd. (JP)

( * ) Notice: Subject to any disclaimer, the term of this patent is extended or adjusted under 35 U.S.C. 154(b) by 0 days.

(21) Appl. No.: 13/505,079

(22) PCT Filed: Oct. 18, 2010

(86) PCT No.: PCT/JP2010/068242
§ 371 (c)(1),
(2), (4) Date: May 22, 2012

(87) PCT Pub. No.: WO2011/052416
PCT Pub. Date: May 5, 2011

(65) Prior Publication Data
US 2012/0222649 A1 Sep. 6, 2012

(30) Foreign Application Priority Data

Oct. 30, 2009 (JP) ................................. 2009-250355

(51) Int. Cl.
*F02M 25/00* (2006.01)
*B01F 3/04* (2006.01)
(Continued)

(52) U.S. Cl.
CPC .............. *B01F 3/04063* (2013.01); *A61L 9/14* (2013.01); *A61L 9/20* (2013.01); *B01F 3/0807* (2013.01);
(Continued)

(58) Field of Classification Search
CPC .... B01F 3/0807; B01F 5/0403; B01F 7/0012; B01F 7/24; F22B 27/16; F23K 5/12
USPC ...... 123/25 E, 25 R, 294, 296, 295, 301, 304, 123/305; 239/424, 425, 466, 338, 340, 398; 261/76, 75, 78.1; 431/208, 210, 4, 9; 417/151
See application file for complete search history.

(56) References Cited

U.S. PATENT DOCUMENTS 3,336,017 A * 8/1967 Kopa ............................. 261/128
4,255,121 A * 3/1981 Sugimoto ..................... 431/208
(Continued)

FOREIGN PATENT DOCUMENTS

JP 62-18524 2/1987
JP 01-151962 6/1989
(Continued)

OTHER PUBLICATIONS

Itoh, S. and Nakamura, K; "Reduction of Diesel Exhaust Gas Emission with Common Rail System"; Denso Technical Review, vol. 7, No. 1, 2002.

*Primary Examiner* — Noah Kamen
*Assistant Examiner* — Long T Tran
(74) *Attorney, Agent, or Firm* — Clark Hill PLC

(57) ABSTRACT

Provided is a gas-liquid mixing nozzle (10) including an internal air discharge path (A), an external air discharge path (D), at least one liquid introduction path (B, C) which is disposed between the internal air discharge path (A) and the external air discharge path (D) and introduces a liquid having water and/or fuel as a main component into a nozzle discharge opening (18), and an impact member (22) with which a mixture of the air and the liquid mixed with each other in the outlets of the internal air discharge path (A) and the liquid introduction path (B, C) collides, the outlet of the internal air discharge path (A) and the outlet of the liquid introduction path (B, C) being disposed on the inside of a nozzle in relation to the nozzle discharge opening (18), and the impact member (22) being disposed between, the outlets of the internal air discharge path (A) and the liquid introduction path (B, C) and the nozzle discharge opening (18). With the above-described configuration, the gas and the liquid may be highly efficiently mixed with each other, and the generation of water droplets of a liquid may be suppressed, thereby producing finer particles.

2 Claims, 6 Drawing Sheets

Figure 1:
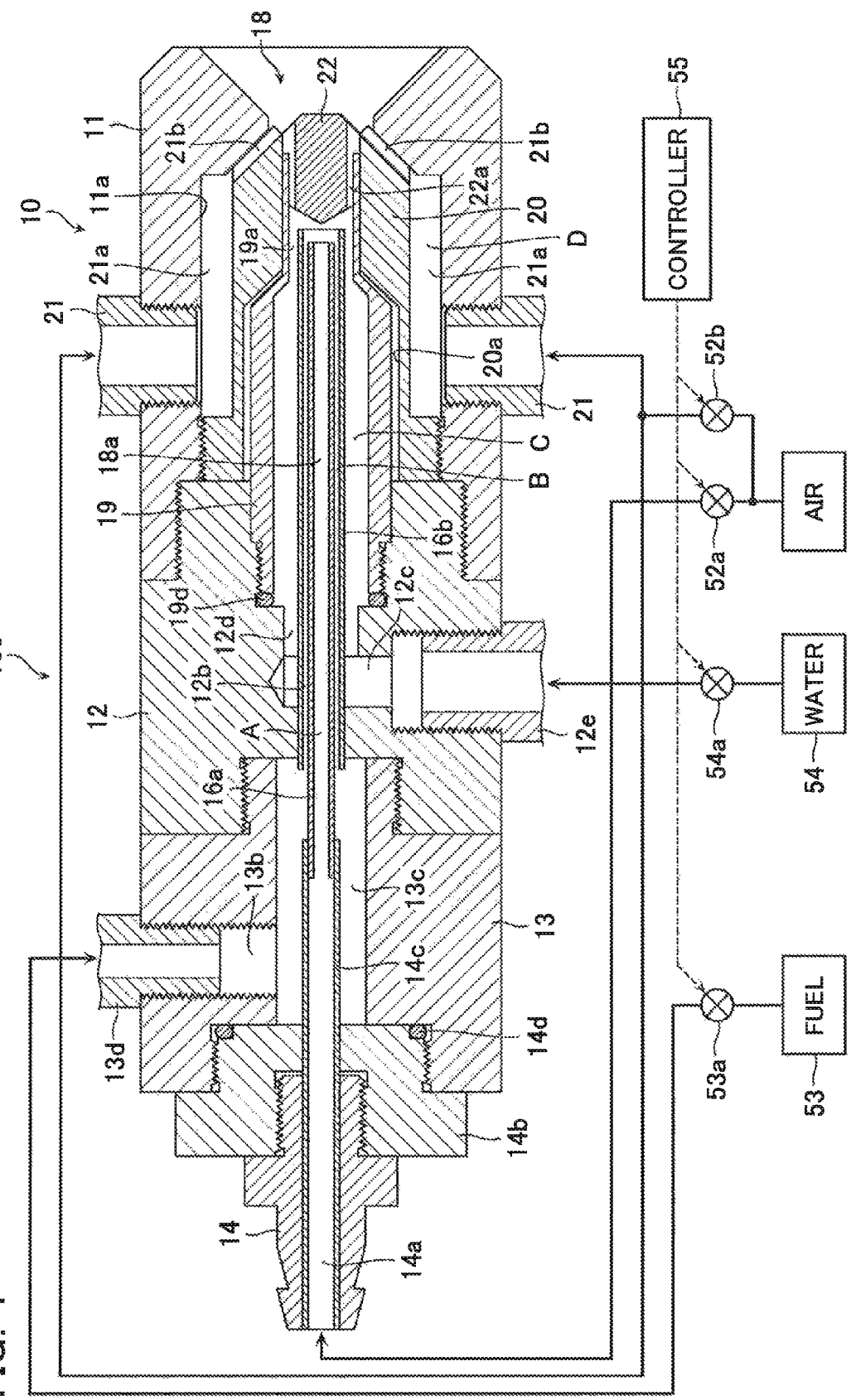

(51) Int. Cl.
  *A61L 9/14* (2006.01)
  *A61L 9/20* (2006.01)
  *B01F 3/08* (2006.01)
  *B01F 5/02* (2006.01)
  *B05B 1/26* (2006.01)
  *B05B 1/34* (2006.01)
  *B05B 7/04* (2006.01)
  *B05B 7/10* (2006.01)
  *F02M 25/022* (2006.01)
  *F23D 11/16* (2006.01)

(52) U.S. Cl.
  CPC ............... *B01F 5/0268* (2013.01); *B05B 1/265* (2013.01); *B05B 1/3415* (2013.01); *B05B 7/0433* (2013.01); *B05B 7/0491* (2013.01); *B05B 7/10* (2013.01); *F02M 25/0225* (2013.01); *F02M 25/0228* (2013.01); *F23D 11/16* (2013.01); *A61L 2209/212* (2013.01); *Y02T 10/121* (2013.01)
  USPC ........ 123/25 E; 123/25 R; 123/294; 239/424; 431/208

(56) References Cited

U.S. PATENT DOCUMENTS

| 4,604,052 | A | * | 8/1986 | Brown et al. .................. 431/168 |
| 5,409,169 | A | * | 4/1995 | Saikalis et al. ................ 239/404 |
| 6,095,113 | A | * | 8/2000 | Nogi et al. ..................... 123/295 |
| 6,491,236 | B1 | * | 12/2002 | Keller ............................. 239/399 |
| 7,687,171 | B2 | * | 3/2010 | Ban et al. ....................... 429/411 |
| 7,814,745 | B2 | * | 10/2010 | Levin et al. ..................... 60/286 |

FOREIGN PATENT DOCUMENTS

| JP | 10-057465 | 3/1998 |
| JP | 2002-355583 | 12/2002 |
| JP | 2006-125407 | 5/2006 |

* cited by examiner

CROSS SECTION OF A-A'

GAS-LIQUID MIXING NOZZLE, AND EMULSION FUEL COMBUSTION SYSTEM AND ENVIRONMENT PURIFICATION LIQUID SPRAY SYSTEM THAT USE THE SAME

TECHNICAL FIELD

The present invention relates to a gas-liquid mixing nozzle capable of efficiently mixing a gas and a liquid with each other, and relates to an emulsion fuel combustion system and an environment purification liquid spray system using the gas-liquid mixing nozzle.

BACKGROUND ART

In recent years, for example, various techniques for purifying exhaust gas of a diesel, engine have been proposed due to the increasing of environment problems. The approach in this type of exhaust gas purification technique is performed, for example, from the viewpoint of improvement in the engine combustion, improvement in the post-processing technique, or improvement in fuel.

Among these viewpoints, as for the improvement in the engine combustion, the improvement in a fuel injection system is regarded as the most important factor, and for example, there has been proposed a technique for realizing and improving a high-pressure injection and a multi-stage injection using a common rail system which is mainly used as the fuel injection system of a diesel automobile (for example, see Non Patent Literature 1).

Further, as for the improvement in the fuel, a technique using emulsion fuel has been developed, and some positive results have been obtained. Furthermore, as a method of reducing nitrogen oxide (NOx) contained in the exhaust gas of a diesel engine, there have been known effective methods such as a method of mixing water into fuel, a method of spraying water to a combustion chamber in addition to fuel, and the like. These methods use the principles in which NOx is reduced with a decrease in the combustion temperature through the mixing of water into fuel and the combustion efficiency is improved by oxygen contained in steam.

RELATED ART DOCUMENT

Non Patent Literature

Non Patent Literature 1: Shohei ITO, Kenzi NAKAMURA, 'Purification of diesel exhaust gas using common rail', Denso technical review, Denso Corporation, May in 2002, Vol. 7, No. 1, p. 20-28

SUMMARY OF INVENTION

Problem to be Solved by the Invention

As described above, in the technical field of the diesel engine, for the purpose of confirming the complete combustion of fuel, the exhaust gas is purified based on the concept in which the fuel injection pressure is extremely improved so as to finely gasify the discharged particles. However, as for the mixture between air (oxygen) and fuel inside the combustion chamber of the diesel engine, the physically complete mixture may not be realized in the related art.

Further, the above-described emulsion fuel has problems, in the viewpoint of cost or management, that a separate fuel production device is needed, an emulsifier for forming stable emulsion needs to be prepared, and a technique of maintaining and managing the optimal state of emulsion fuel is needed.

Furthermore, as for the above-described mixing of water, for example, a water spray device is separately needed in order to spray water into the combustion chamber in addition to the purpose of the fuel injection. Then, since the NOx reduction effect is not sufficiently obtained, water adheres to the front end of the nozzle so that water droplets are generated, emitted black smoke increases, or the fuel consumption rate is degraded depending on the performance of the water spray device, it is not easy to optimize the design of the water spray device.

The present invention has been made in view of the above-described problems, and has an object of realizing a gas-liquid mixing nozzle capable of efficiently mixing a gas and a liquid with each other and producing finer particles by suppressing the generation of water droplets of a liquid, and to providing an emulsion fuel combustion system and an environment purification liquid spray system using the gas-liquid mixing nozzle.

Means for Solving the Problem

A first gas-liquid mixing nozzle according to the present invention includes: an internal air discharge path which discharges air toward a center portion of a nozzle discharge opening; an external air discharge path which discharges air from the outer edge portion of the nozzle discharge opening; at least one liquid introduction path which is disposed between the internal air discharge path and the external air discharge path and introduces a liquid having water and/or fuel as a main component into the nozzle discharge opening; and an impact member with which a mixture of the air and the liquid mixed with each other in outlets of the internal air discharge path and the liquid introduction path collides, the outlet of the internal air discharge path and the outlet of the liquid introduction path being disposed on the inside of a nozzle in relation to the nozzle discharge opening, and the impact member being disposed between the outlets of the internal air discharge path and the liquid introduction path and the nozzle discharge opening.

Further, a second gas-liquid mixing nozzle according to the present invention includes: an internal air discharge path which discharges air toward a center portion of a nozzle discharge opening; an external air discharge path which discharges air from the outer edge portion of the nozzle discharge opening; at least one liquid introduction path which is disposed between the internal air discharge path and the external air discharge path and introduces a liquid having water and/or fuel as a main component into the nozzle discharge opening; and an impact member with which a mixture of the air and the liquid mixed with each other in outlets of the internal air discharge path and the liquid introduction path collides, the impact member including a penetration hole formed from the outlet of the internal air discharge path to the front end portion of the impact member.

Furthermore, a third gas-liquid mixing nozzle according to the present invention includes: an internal air discharge path which discharges air toward a center portion of a nozzle discharge opening; an external air discharge path which discharges air from the outer edge portion of the nozzle discharge opening; at least one liquid introduction path which is disposed between the internal air discharge path and the external air discharge path and introduces a liquid having water and/or fuel as a main component into the nozzle discharge opening; and an impact member with which a mixture of the air and the liquid mixed with each other in outlets of the internal air discharge path and the liquid introduction path collides, the impact member rotating about the a nozzle central axis by the force of wind of the mixture of the air and the liquid.

In the first gas-liquid mixing nozzle according to the present invention, the impact member is formed in a conical shape of which the end portion facing the outlet of the internal air discharge path is formed as an outlet-side apex, and a side surface is provided with the guide grooves which introduce the mixture of the air and the liquid mixed with each other in the outlets of the internal air discharge path and the liquid introduction path and are inclined with respect to the central axis so as to apply a rotational force to the mixture.

In the second gas-liquid mixing nozzle according to the present invention, the impact member includes a side surface which is narrowed in a taper shape toward the nozzle discharge opening and guide grooves which are formed in the side surface so as to extend in the direction of the central axis of the nozzle, the mixture of the air and the liquid being mixed in the outlets of the internal air discharge path and the liquid introduction path being made to flow along the guide grooves of the side surface.

In the third gas-liquid mixing nozzle according to the present invention, the impact member includes a side surface which is narrowed in a taper shape toward the nozzle discharge opening and guide grooves which are formed in the side surface so as to extend in a direction inclined with respect to the central axis of the nozzle, the rotational force being applied from the mixture by introducing the mixture of the air and the liquid mixed in the outlets of the internal air discharge path and the liquid introduction path into the guide grooves.

An emulsion fuel combustion system according to the present invention includes: an air supply source which supplies air; a fuel supply source which supplies fuel; a combustion temperature reduction liquid supply source which supplies a liquid having water as a main component and reducing the combustion temperature; and the gas-liquid mixing nozzle according to the above-described invention, the gas-liquid mixing nozzle being assembled to a burner device body.

Another emulsion fuel combustion system according to the present invention includes: an air supply source which supplies air; a fuel supply source which supplies fuel; a combustion temperature reduction liquid supply source which supplies a liquid having water as a main component and reducing the combustion temperature; and the gas-liquid mixing nozzle according to the above-described invention, the gas-liquid mixing nozzle being assembled to a fuel injection device of an internal combustion engine, the air, the fuel, and the liquid being respectively introduced from the air supply source, the fuel supply source, and the combustion temperature reduction liquid supply source, and the air, the fuel, and the liquid for forming a mixture gas completely burned inside a combustion chamber of the internal combustion engine being discharged.

An environment purification liquid spray system according to the present invention includes: an air supply source which supplies air; an environment purification liquid supply source which supplies a liquid having water as a main component and used for environment purification; the gas-liquid mixing nozzle according to the above-described invention; an ultraviolet ray irradiation unit which irradiates an ultraviolet ray from the gas-liquid mixing nozzle to sprayed water; and a dispersion unit which disperses the sprayed water irradiated with the ultraviolet ray by the ultraviolet ray irradiation unit into the atmosphere.

In the environment purification liquid spray system according to the present invention, the liquid preferably contain molecules and atoms containing carbon, catechin, theanine, selfeel, a leaf milky liquid of a mulberry, and nano particles of a pyrethrum and having an insect killing and sterilizing effect.

Further, in the environment purification liquid spray system according to the present invention, the air preferably contain ozone ($O_3$).

Effects of Invention

According to the present invention, it is possible to provide a gas-liquid mixing nozzle capable of efficiently mixing a gas and a liquid with each other and generating finer particles by suppressing the generation of water droplets of a liquid. Further, it is possible to provide a novel emulsion fuel combustion system and a novel environment purification liquid spray system using the gas-liquid mixing nozzle according to the present invention.

BRIEF DESCRIPTION OF DRAWINGS

FIG. 1 is a diagram illustrating an emulsion fuel combustion system configured as a burner device, which illustrates a cross section of a gas-liquid mixing nozzle according to a first embodiment of the present invention.

FIGS. 2A and 2B are diagrams illustrating an impact member of the gas-liquid mixing nozzle, where FIG. 2A is a cross-sectional view and FIG. 2B is a front view.

FIG. 3 is an external perspective view illustrating the impact member of the gas-liquid mixing nozzle.

FIG. 4 is a cross-sectional view illustrating a gas-liquid mixing nozzle according to a second embodiment of the present invention.

FIG. 5 is a cross-sectional view illustrating a gas-liquid mixing nozzle according to a third embodiment of the present invention.

FIGS. 6A and 6B are diagrams illustrating an impact member of the gas-liquid mixing nozzle, where FIG. 6A is a side view and FIG. 6B is a cross-sectional view.

FIGS. 7A and 7B are diagrams illustrating an environment purification liquid spray system according to another embodiment of the present invention, where FIG. 7A is a side view and FIG. 7B is a front view.

BEST MODE FOR CARRYING OUT THE INVENTION

Hereinafter, referring to the accompanying drawings, preferable embodiments of a gas-liquid mixing nozzle according to the present invention and an emulsion fuel combustion system and an environment purification liquid spray system using the gas-liquid mixing nozzle will be described in detail.

First Embodiment

FIG. 1 is a diagram illustrating an emulsion fuel combustion system which uses a gas-liquid mixing nozzle according to a first embodiment.

A gas-liquid mixing nozzle 10 is used in, for example, an emulsion fuel combustion system 100 serving as a burner device. Specifically, the emulsion fuel combustion system 100 includes the gas-liquid mixing nozzle 10 which is assembled to a main body of an existing burner device (not illustrated) and a unit which supplies the air, the fuel, and the water to the gas-liquid mixing nozzle 10.

As illustrated in the cross section of FIG. 1, the gas-liquid mixing nozzle 10 includes a cylindrical front member 11, an intermediate member 12, and a rear member 13 of which the outer diameters are approximately equal to each other and the inner diameters are different from each other. These members 11 to 13 are formed of an iron-based or iron-copper-based metal material, and are connected to each other in a manner such that male screws and female screws provided in the connection positions thereof are screw-connected to each other.

As for the front member 11, the front end portion is provided with a bowl-like nozzle discharge opening 18 which is widened forward, and a cylindrical impact member support cylinder 20 is coaxially accommodated in an internal space 21a. The rear side of the nozzle discharge opening 18 of the front member 11 is formed in a bowl shape so as to be widened backward, and the conical front end of the impact member support cylinder 20 faces the rear side with a predetermined gap interposed therebetween. An intermediate cylinder 19 is coaxially disposed inside the impact member support cylinder 20. The rear end of the intermediate cylinder 19 is liquid-tightly fixed to the front end side of the intermediate member 12 through an O-ring 19d by screw-connecting. The front end of the intermediate cylinder 19 extends to the front end portion of the impact member support cylinder 20, and an impact member 22 to be described later is attached to the front end portions of the intermediate cylinder 19 and the impact member support cylinder 20. A front air coupling 21 which communicates with an internal space 21a is attached to two facing side surfaces of the front member 11. A pipe 16b is coaxially disposed in an internal space 19a of the intermediate cylinder 19. As for a pipe 16b, the front end side extends to the vicinity of the impact member 22, and the rear end side is press-inserted into the intermediate member 12. A pipe 16a is further coaxially disposed inside the pipe 16b. As for the pipe 16a, the front end side extends to the vicinity of the front end portion of the pipe 16b, and the rear end side extends to the inside of the rear member 13.

As for the intermediate member 12, the front end side is provided with an internal space 12d of which the inner diameter is larger than the outer diameter of the pipe 16b, and the internal space 12d communicates with the internal space 19a of the intermediate cylinder 19. A water nozzle coupling 12e which communicates with the internal space 12d is attached to a water introduction hole 12c which is formed in the side surface of the intermediate member 12.

As for the rear member 13, a fuel nozzle coupling 13d which communicates with an internal space 13c is mounted into a fuel introduction hole 13b formed in the side surface, and a rear air coupling 14 is attached to the rear end portion thereof through an O-ring 14d and a coupling joint portion 14b. A pipe 14c is press-inserted into the rear air coupling 14. The front end side of the pipe 14c is connected to the rear end side of the pipe 16a.

Then, an internal air discharge path A is formed by the rear air coupling 14, an internal space 14a of the pipe 14c, and an internal space 18a of the pipe 16a, a fuel introduction path B is formed by the fuel nozzle coupling 13d, the fuel introduction hole 13b, the internal space 13c, and a space 12b between the pipes 16a and 16b, a water introduction path C is formed by the water nozzle coupling 12e, the water introduction hole 12c, the internal space 12d, and the internal space 19a, and an external air discharge path D is formed by the front air coupling 21, the internal space 21a, and a gap between the impact member support cylinder 20 and the front member 11.

Figure 2A:
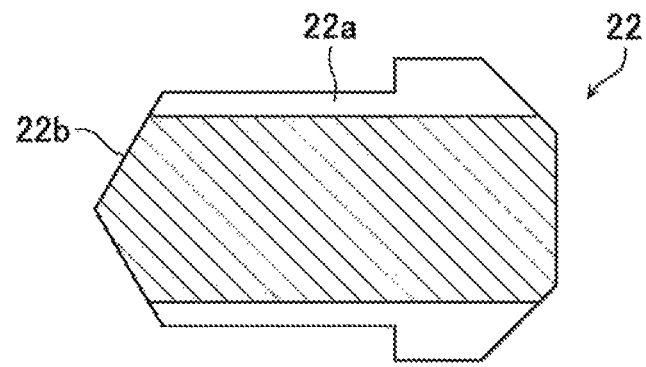
Figure 2B:
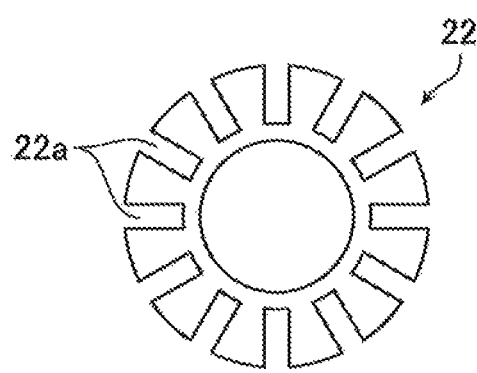
Figure 3:
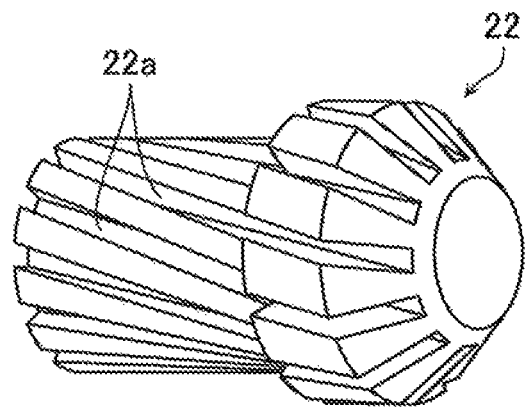

Next, the impact member 22 will be described. FIG. 2A is a cross-sectional view of the impact member 22 and FIG. 2B is a front view thereof, and FIG. 3 is an external perspective view. As illustrated in these drawings, since the impact member 22 is press-inserted into the intermediate cylinder 19, the rear end side is formed in a cylindrical shape with a small diameter, a plurality of guide grooves 22a are formed in the side surface in the circumferential direction at a predetermined interval so as to extend in a spiral shape or in the direction slightly inclined with respect to the central axis, and then a conical rear end portion 22b is provided. The guide grooves 22a are used to apply a rotational force to a mixture gas while introducing the mixture gas colliding with the rear end side.

As for the gas-liquid mixing nozzle 10 with the above-described configuration, under the control of a controller 55, air which is supplied from air pumps 52a and 52b serving as an air supply source supplying air is introduced into the inner air introduction path A and the outer air introduction path B through the front air coupling 21 and the rear air coupling 14, fuel such as gasoline, diesel, and oil which is supplied from a fuel tank 53 serving as a fuel supply source by a pump 53a is introduced into the fuel introduction path B through the fuel nozzle coupling 13d, and water which is supplied from a water tank 54 serving as a water supply source by a pump 54a is introduced into the water introduction path C through the water nozzle coupling 12e.

According to the emulsion fuel combustion system with the above-described configuration, the air which is introduced into the internal air discharge path A is mixed with the fuel which passes through the fuel introduction path B on the outside thereof at the front end of the pipe 16a, so that the mixture becomes a mist, and then the mixture is mixed with the water at the portion joined to the water introduction path C. Almost at the same time, the mixture of water, fuel, and air collides with the impact member 22, so that the mixture becomes mist with finer particles. The mixture which collides with the impact member 22 receives a rotational force while passing through the guide grooves 22a of the impact member 22, and then is mixed with the air which is discharged from the external air discharge path D. The air which is discharged from the external air discharge path D having a conical discharge opening formed according to an angle of 45° between the front member 10 and the front end of the impact member support cylinder 20 is expanded and discharged while rotating in a conical shape at an angle of about 45° along the bowl-like side surface of the nozzle discharge opening 18. In this way, according to the gas-liquid mixing nozzle 10 of the embodiment, since the mixture of the air, the fuel, and the water collides with the impact member 22, emulsion fuel with extremely delicate particles is produced.

Furthermore, since the operations of the respective pumps 52a, 52b, 53a, and 54a are controlled by the controller 55 having a CPU and the like, it is possible to discharge the air, the fuel, and the water from the gas-liquid mixing nozzle 10 in consideration of the optimal mixture ratio or the optimal discharge amount. Further, the water tank 54 may be formed so that magnesium (Mg) supplied from a magnesium tank (not illustrated) is mixed with the water inside the water tank.

Furthermore, the fuel which is supplied from the fuel tank 53 or the air which is supplied from the air pumps 52a and 52b may be mixed with carbon supplied from a carbon tank (not illustrated). As the fuel, kerosene, light oil, A-type heavy oil, cooking oil, or the like may be used in addition to the above-described examples. As the water, tap water may be used, but it is desirable to use, for example, water which passes through a filter so as to perform chlorine removal or the like thereon.

As the air, compressed air having an air pressure of 1 kgf/cm² at maximum may be used, and the flow rate thereof was set, for example, from 70 l/min to 100 l/min in the emulsion fuel combustion system 100. However, the amount of air may be arbitrarily changed by the amount of emission, heat or the like of a burner.

Further, the air which is discharged from the gas-liquid mixing nozzle 10, that is, the air which is discharged from the internal air discharge path A and the external air discharge path D may contain, for example, carbon which is formed so as to have a diameter of micron order or nano order. In this way, when the mixture of carbon and air is discharged, the consumption of fossil fuel may be reduced as much as possible, and hence a high amount of heat may be ensured.

Furthermore, when an ozone generator (not illustrated) is disposed adjacent to the air pumps 52a and 52b so that ozone ($O_3$) is mixed with the supplied air, there may be a contribution to the improvement in combustion efficiency. Further, as the water which is supplied from the water tank 54 to the gas-liquid mixing nozzle 10, the water was mixed with magnesium in order to maintain the more efficient combustion and explosive power.

The magnesium may be produced from sea water. Furthermore, since the magnesium contributes to a reduction in the consumption amount of fossil fuel, it is a desirable material for the environment. However, the element materials which are mixed with water are not limited to the magnesium, and other elements having an oxidization promoting effect may be mixed with the water.

Here, in a case of kerosene, it is desirable to set the consumption ratio between fuel and water so that 50% of water is consumed with respect to 50% of kerosene or 60% of water is consumed with respect to 40% of kerosene. However, since the mixture ratio between fuel and water may be arbitrarily determined depending on the use condition or the like, the mixture ratio is not limited thereto.

When the emulsion fuel combustion system 100 illustrated in FIG. 1 is operated in the above-described implementation condition, there is an effect that fuel is reduced by about 15% compared to the existing burner device. Furthermore, there is an effect that the discharge amount of $CO_2$ is reduced by about 15%. Accordingly, according to the emulsion fuel combustion system 100 with the burner device using the gas-liquid mixing nozzle 10 of the first embodiment, it is possible to construct a fuel combustion system which is satisfactory from the viewpoint of environment.

Then, since the gas-liquid mixing nozzle 10 according to the first embodiment is formed by the above-described configuration, the air, the fuel, and the water are mixed with each other inside the nozzle in advance, and the mixture is discharged to the front side while being expanded in a conical shape at a predetermined angle with respect to the discharge direction. That is, the emulsion fuel is not obtained by the mixture at the nozzle discharge opening 18, but the mixture inside the nozzle in the optimal state.

Furthermore, since the impact member 22 is disposed inside the nozzle discharge opening 18 and the mixture is further discharged by the external air discharge paths 21b and 21b, there is an effect that water droplets of a mixture are not attached to the front end surface of the impact member 22 and the water droplets are not generated.

Thus, according to the gas-liquid mixing nozzle 10 of the first embodiment, it is possible to completely mix fuel, air, and water with each other and discharge the mixture thereof, where in the related art, it is difficult to completely mix fuel, air, and water with each other. Further, there is no need to provide a technique of maintaining and managing the optimal state of emulsion fuel. Furthermore, in the gas-liquid mixing nozzle 10 according to the first embodiment, there is no need to provide the water spray device which is needed in the technique of mixing water of the related art, and hence it is possible to realize the gas-liquid mixing nozzle with a low-cost and simple configuration.

Furthermore, as the condition in which the air, the fuel, and the water are optimally mixed with each other by using the gas-liquid mixing nozzle 10 according to the first embodiment, for example, when the air pressure of the air discharged from the internal air discharge path A is denoted by $P_1$ and the air pressure of the air discharged from the external air discharge path D is denoted by $P_2$, the inequation of $P_1 \geq P_2$ is preferably established.

Basically, since the air which is discharged from the internal air discharge path A is discharged forward in the straight line direction, the air is sufficiently mixed with fuel and is further mixed with water, and also serves as a carrier which moves the fuel and the water forward. On the other hand, since the air which is discharged from the external air discharge path D is discharged so as to draw a conical shape in a predetermined angle direction, it is possible to exhibit a function of appropriately discharging the mixture. As a result of the inventor's study for the air pressure condition appropriately exhibiting the respective functions, it is confirmed that it is desirable that the inequation of $P_1 \geq P_2$ be established.

While the preferable embodiment of the present invention has been described, the technical scope of the invention is not limited to the scope of the first embodiment. In the first embodiment, various modifications or improvements may be made. For example, each of the fuel and the water which are discharged and introduced between the internal air discharge path 18a and the external air discharge paths 21b and 21b is discharged in a single layer in the first embodiment, but when the introduction path for the fuel or the water is made complicated and the fuel or the water is discharged in a multiple-layer structure, the higher mixture ratio may be realized.

Further, the air, the fuel, and the water are mixed with each other in this order inside the gas-liquid mixing nozzle 10, but they may be mixed with each other in order of the air, the water, and the fuel or in other orders. In this case, when the paths for the air, the fuel, and the water introduced into the nozzle are changed, these orders may be easily obtained.

Furthermore, the distance between the air, the fuel, and the water to be mixed with each other inside the nozzle discharge opening 18 and the distance between the mixture of the air, the fuel, and the water to be discharged and air in the nozzle discharge opening 18 may be arbitrarily changed, and according to the theory, the mixing efficiency may be further improved when these gaps are closer to each other. The distance between the gas and the liquid in the nozzle discharge opening 18 may be arbitrarily changed depending on the use condition.

Furthermore, in the first embodiment, when the discharge grooves 22a of the conical member 22 are obliquely arranged, the mixture which is discharged from the end portion of the nozzle discharge opening 18 is discharged while receiving the rotational force generated by the action of the discharge groove 22a. However, for example, when a groove structure having a whirl shape is provided inside the paths of the external air discharge paths 21b and 21b, the rotational force may be further applied to air.

In such a case, air, fuel and a liquid such as water may be further efficiently mixed with each other, and a gas and a liquid may be more effectively mixed with each other. Further, the angle in which the mixture or the air is discharged may be arbitrarily changed, and may be changed to the optimal angle depending on the use condition and the like of the gas-liquid mixing nozzle 10.

Furthermore, in the first embodiment, in the vicinity of the end portion near the nozzle discharge opening 18 of the internal air discharge path A on the inside of the nozzle discharge opening 18, the impact member 22 which includes conical shape and has an apex directed toward the end portion is installed inside the nozzle discharge opening 18. However, as for the conical member 22, an impact member may be used which applies an impact force by the collision with the air or the liquid discharged at a high pressure and mixes the air or the liquid in the more delicate mixture state.

Then, as for the shape in which the impact member is formed, the present invention is not limited to the conical shape, and any shape capable of exhibiting the operation and effect of the impact generating and mixing operation may be adopted. Further, as for the air pressure of the air, the mixing efficiency of air with respect to fuel or water further improves as the air pressure becomes higher, so that it becomes finely gasified, thereby improving the combustion efficiency.

Furthermore, these condition values may be controlled through both the air-fuel ratio control and the control using a microcomputer, and the technique of completely burning emulsion fuel may be established by the gas-liquid mixing nozzle of the present invention. Here, the emulsion fuel combustion system 100 using the gas-liquid mixing nozzle 10 according to the first embodiment has been described by exemplifying the case of the application to the burner device as described above, but the emulsion fuel combustion system 100 may be applied to not only an opened system such as a burner device, but also a closed system such as an internal combustion engine.

That is, a configuration may be adopted in which the gas-liquid mixing nozzle 10 according to the first embodiment is assembled to the fuel injection device of the existing internal combustion engine, air, fuel, and liquid are respectively introduced from the air supply source, the fuel supply source, and the combustion temperature reduction liquid supply source, and the air, the fuel, and the liquid used for forming a mixture gas which may be completely burned inside the combustion chamber of the internal combustion engine is discharged.

Furthermore, the operation condition of the internal combustion engine may be arbitrarily set depending on the use condition, the specification, or the like of the internal combustion engine. As the advantageous point of the emulsion fuel combustion system serving as the internal combustion engine using the gas-liquid mixing nozzle 10 according to the present invention, since water may be discharged like a mist and the generation of water droplets may be suppressed, it is possible to reliably suppress the combustion temperature and purify the inside of the combustion chamber (engine room) by adjusting particularly the amount of water.

Through this effect, nitrogen oxide (NOx) may be suppressed and the amount of NOx in the exhaust gas may be reduced. Furthermore, as for the method of preventing the degradation of the engine due to the introduction of water into the engine room, the degradation of the engine may be prevented by stopping the discharge of water for several seconds before the engine is stopped. This control may be easily performed through the control using a microcomputer.

Second Embodiment

Figure 4:
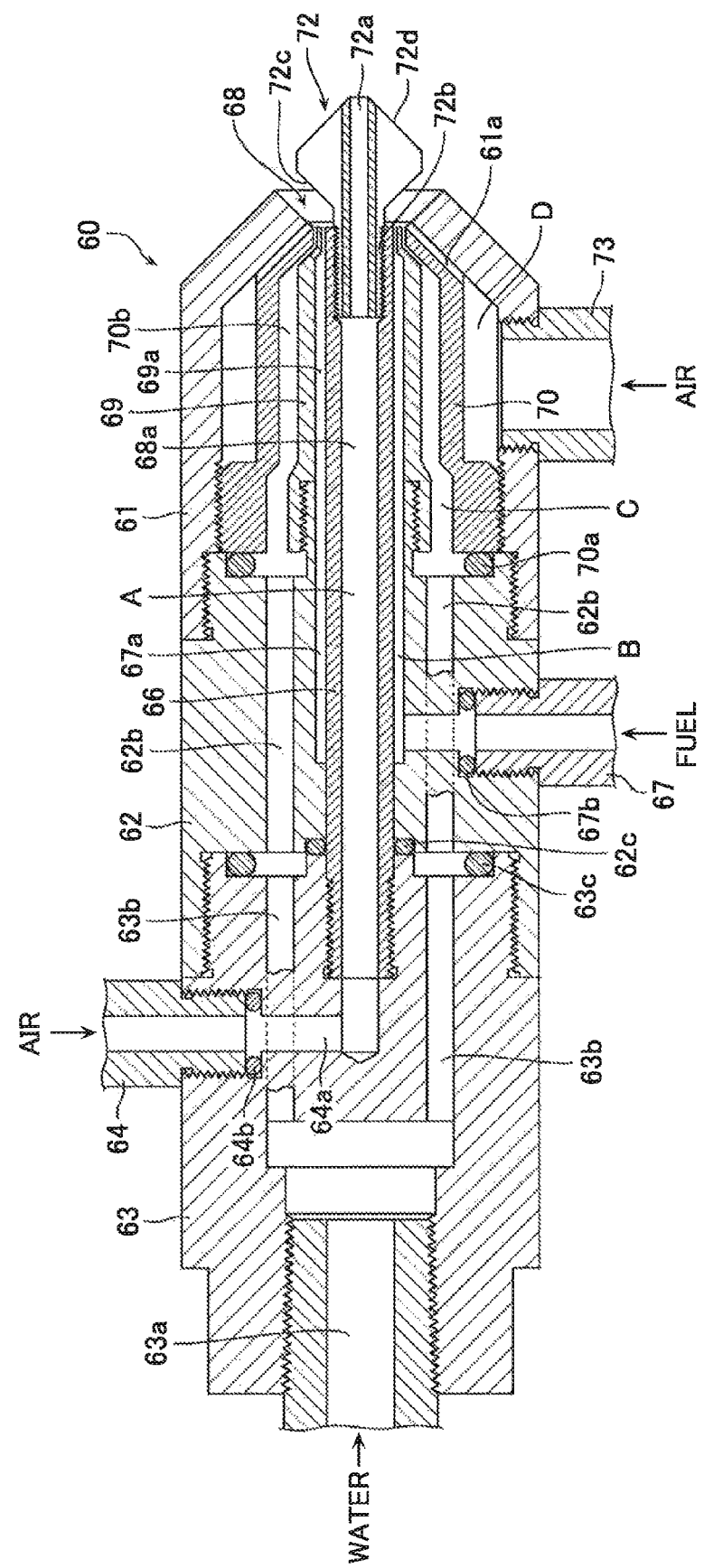

FIG. 4 is a cross-sectional view illustrating an example of a gas-liquid mixing nozzle according to a second embodiment of the present invention.

As illustrated in FIG. 4, a gas-liquid mixing nozzle 60 includes a cylindrical front member 61, an intermediate member 62, and a rear member 63 of which the outer diameters are approximately equal to each other and the inner diameters are different from each other. These members 61 to 63 are formed of an iron-based or iron-copper-based metal material, and are connected to each other in a manner such that male screws and female screws provided in the connection positions thereof are screw-connected to each other through O-rings 62a, 63a, and 70a.

As for the front member 61, the front end portion is provided with a bowl-like nozzle discharge opening 68 which is widened forward, and a cylindrical intermediate cylinder 70 is coaxially accommodated in an internal space 61a. The rear side of the nozzle discharge opening 68 of the front member 61 is formed in a bowl shape so as to be widened backward, and the conical front end of the intermediate cylinder 70 faces the rear side with a predetermined gap interposed therebetween. An intermediate cylinder 69 is coaxially disposed inside the intermediate cylinder 70. The rear end of the intermediate cylinder 69 is screw-connected to the front end side of the intermediate member 62. The front end of the intermediate cylinder 69 extends to the front end portion of the intermediate cylinder 70. A front air coupling 73 which communicates with the internal space 61a is attached to the side surface of the front member 61. A pipe 66 is coaxially disposed in the internal space 69a of the intermediate cylinder 69. As for the pipe 66, the front end side extends to the front end portions of the intermediate cylinders 69 and 70, and the front end portion supports an impact member 72 to be described later. The rear end side of the pipe 66 is screw-connected to the front end portion of the rear end member 63.

As for the intermediate member 62, the front end side is provided with an internal space 67a of which the inner diameter is larger than the outer diameter of the pipe 66, and the internal space 67a communicates with the internal space 69a of the intermediate cylinder 69. A fuel nozzle coupling 67 which communicates with the internal space 67a is attached to the side surface of the intermediate member 62 through an O-ring 67b.

As for the rear member 63, a rear air coupling 64 which communicates with an internal space 68a of the pipe 66 is attached to the rear air introduction hole 64a formed in the side surface through an O-ring 64b, and a water nozzle coupling 63a is attached to the rear end portion.

The impact member 72 which is attached to the front end of the nozzle includes a conical front end surface 72d, a conical impact surface 72c which is continuous to the front end surface 72d and has an apex in the direction opposite to the front end surface 72d, a plurality of guide grooves 72b which are formed in the side surface so as to extend in the axial direction, and a center hole 72a which is formed along the axis. As for the center hole 72a, the rear end thereof communicates with the internal space 68a of the pipe 66.

Then, the internal air discharge path A is formed by the rear air coupling 64, the rear air introduction hole 64a, the internal space 68a of the pipe 66, and the guide groove 72b of the impact member 72, the fuel introduction path B is formed by the fuel nozzle coupling 67 and the internal spaces 67a and 69a, the water introduction path C is formed by the water nozzle coupling 63a and internal spaces 63b, 62b, and 70b, and the external air discharge path D is formed by the front air coupling 73 and the internal space 61a.

According to the gas-liquid mixing nozzle 60 with such a configuration, the air introduced into the internal air discharge path A, the fuel introduced into the fuel introduction path B on the outside thereof, the water introduced into the water introduction path C, and the air introduced into the external air discharge path D are mixed with each other in front of the impact surface 72c of the impact member 72, and collide with the impact surface 72c. At this time, since the air is discharged from the external air discharge path D at an angle in which the air perpendicularly collides with the impact surface 72c which is formed in a taper shape of about 45°, the mixture becomes finer particles.

Further, since the air which is introduced into the internal air discharge path A is discharged to the front end side of the nozzle through the center hole 72a of the impact member 72, no water droplet stays in the front end of the impact member 72, thereby preventing the generation of water droplets.

Thus, even in the gas-liquid mixing nozzle 60 according to the second embodiment, the complete mixture between fuel, air, and water which is difficult to be accomplished in the related art may be performed. Further, there is no need to provide a technique of maintaining and managing the optimal state of emulsion fuel. Furthermore, even in the gas-liquid mixing nozzle 60 according to the second embodiment, there is no need to provide the water spray device of the related art, and hence it is possible to realize the gas-liquid mixing nozzle with a low-cost and simple configuration.

Furthermore, as the condition of the air pressure when the air, the fuel, and the water are optimally mixed with each other by using the gas-liquid mixing nozzle 60 according to the second embodiment, when the air pressure of the air discharged from the internal air discharge path 68a is denoted by $P_1$ and the air pressure of the air discharged from the external air discharge path 61a is denoted by $P_2$, it is desirable that the inequation of $P_1 \geq P_2$ be established as in the above-described gas-liquid mixing nozzle 10.

Basically, since the air which is discharged from the internal air discharge path 68a is discharged forward in a straight line direction so as to draw a conical shape in an angular direction of 45°, the air serves as a carrier which moves the mixture of the fuel and the water forward. On the other hand, the air which is discharged from the external air discharge path 61a is discharged forward so as to draw a conical shape in an angular direction of 45°. At the same time, the air is discharged in a rotating manner when a spiral groove is formed, which further exhibits a function of appropriately mixing the fuel and the water with each other.

Furthermore, the technical scope of the present invention is not limited to the scope of the second embodiment. In the second embodiment, various modifications or improvements may be made. For example, each of the fuel and the water which are discharged from the internal air discharge path 68a and the external air discharge path 61a in the parallel direction and introduced in between air layers is discharged in a single layer in the second embodiment, but when the introduction path for the fuel or the water is made complicated and the fuel or the water is discharged in a multiple-layer structure, the higher mixture ratio may be realized.

Further, in the gas-liquid mixing nozzle 60, the air, the fuel, and the water are mixed with each other in this order from the center portion, but they may be mixed with each other in order of the air, the water, and the fuel or in other orders. In this case, when the paths for the air, the fuel, and the water introduced into the nozzle are changed, these orders may be easily obtained.

Furthermore, the distance between the air and the fuel, or between the air and the water to be discharged in the nozzle discharge opening may be arbitrarily changed, and according to the theory, the mixture efficiency may be further improved as these gaps are closer to each other. The distance between the gas and the liquid in the nozzle discharge opening may be arbitrarily changed depending on the use condition and the like.

Further, in the second embodiment, the air which is discharged from the external air discharge path 61a is discharged with a rotational force generated by the action of the guide groove. However, for example, when a groove structure having a whirl shape is provided inside the path of the external air discharge path 61a, the rotational force may be applied to the air. With such a structure, the fuel and the liquid may be further efficiently mixed with each other, and hence the gas and the liquid may be further effectively mixed with each other.

Furthermore, in the second embodiment, the discharged air is discharged forward so as to draw a conical shape in an angular direction of 45°. However, the discharge angle may be arbitrarily changed, and may be changed to the optimal angle depending on the use condition and the like of the gas-liquid mixing nozzle 60.

Furthermore, in the second embodiment, a case has been described in which the tapered member 72 having a taper portion is formed in the end portion of the nozzle discharge opening 68 of the internal air discharge path 68a so that the side surface 72c is narrowed in a taper shape toward the nozzle discharge opening 68 in the air discharge direction. However, as the tapered member 72, an impact member may be used which applies an impact force by the collision with the air or the liquid discharged at a rapid and strong pressure and scatters the air or the liquid as a fine mist-like material.

Third Embodiment

Figure 5:
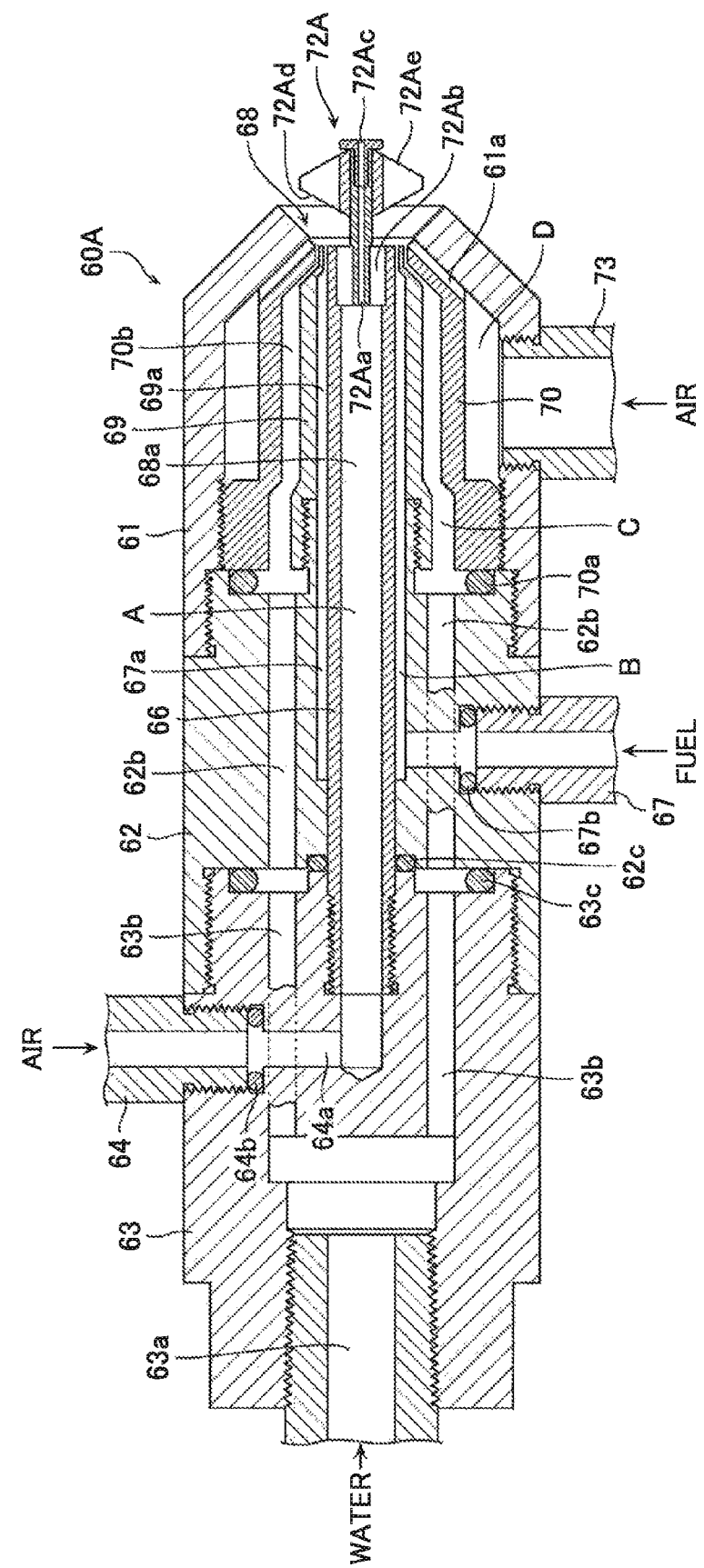
Figure 6A:
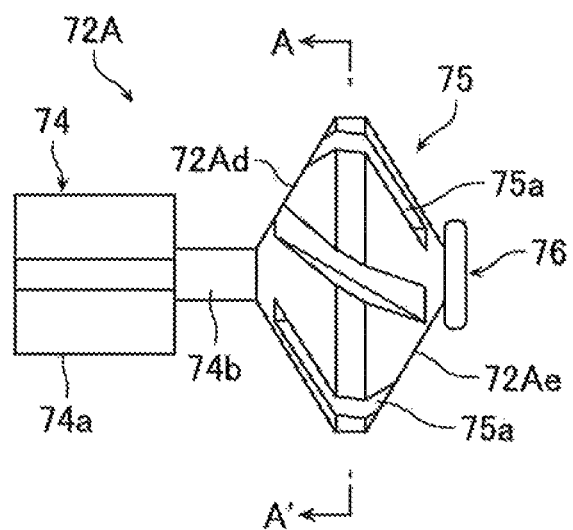
Figure 6B:
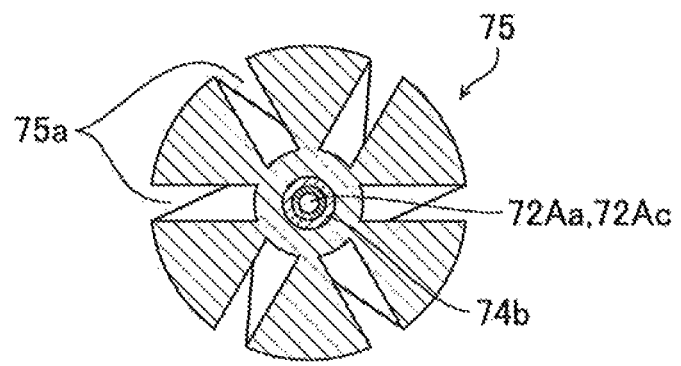

FIG. 5 is a cross-sectional view illustrating an example of a gas-liquid mixing nozzle according to a third embodiment of the present invention. Further, FIG. 6 is a diagram illustrating an example of the impact member of the gas-liquid mixing nozzle, where in particular, FIG. 6A is a side view and FIG. 6B is a cross-sectional view. Furthermore, since the gas-liquid mixing nozzle according to the third embodiment may have the similar configuration to that of the gas-liquid mixing nozzle 60 according to the second embodiment, the same reference numerals will be given to the same components and the description thereof will not be repeated.

As illustrated in FIG. 5, a gas-liquid mixing nozzle 60A according to the third embodiment includes three members, a front member 61, an intermediate member 62, and a rear member 63 as in the gas-liquid mixing nozzle 60 according to the second embodiment. Since the configuration of the paths formed in the respective members 61 to 63, the component such as connected couplings, or the operation and effect or the application example of the nozzle are similar to each other, these will not be described herein.

On the other hand, as for the gas-liquid mixing nozzle 60A, the structure of an impact member 72A formed in the air discharge direction at the end portion of the nozzle discharge opening 68 of the internal air discharge path 68a is different from that of the impact member 72 of the gas-liquid mixing nozzle 60 of the foregoing example. That is, as illustrated in FIG. 6A, the impact member 72A which is attached to the gas-liquid mixing nozzle 60A includes a rotation portion 75, a journal portion 74, and an accumulation portion 76.

As for the impact member 72A, an attachment portion 74a having a cross shape in section of the rear end side journal portion 74 is press-inserted and fitted into the front end side of the center air pipe 66, and the rotatable top-shaped rotation portion 75 is attached to a shaft portion 74b of the journal portion 74. Furthermore, the accumulation portion 76 which prevents the separation of the rotation portion 75 is press-inserted into the front end side of the shaft portion 74, and the impact member is attached to the end portion of the nozzle discharge opening 68.

As for the rotation portion 75, the side surface is provided with guide grooves 75a which discharge the mixture of the air, the fuel, and the water colliding with the impact member 72A so as to rotate in a conical shape in the air discharge direction toward the nozzle discharge opening 68. As for the rotation portion 75, aside surface 72Ad is narrowed in a taper shape toward the nozzle discharge opening 68, a side surface 72Ae has an top external shape which is narrowed in a taper shape toward the front end side (that is, the rear end side and the front end side are formed in a taper shape), and the center portion of the nozzle discharge opening 68 is used as a rotation axis.

As for the guide grooves 75a, as illustrated in FIGS. 6A and 6B, the guide grooves are formed in a spiral shape near the nozzle discharge opening 68, for example, in a twisted state with an angle of about 30°. Further, the cross-shaped portions of the attachment portion 74a of the journal portion 74 are formed so as to have thicknesses different from each other. Accordingly, the flow rate of the air which is discharged from the internal air discharge path 68a may be changed and the turning force of the rotation portion 75 may be improved. Also, the mixture of the liquid and the liquid, the gas and the liquid, the gas and the gas, and the like may be promoted, so that the mist-like mixture may be obtained.

The journal portion 74 includes a first impact member side air discharge path 72Aa which is formed at the center portion thereof so as to rotatably journal the rotation portion 75 and to communicate with the internal air discharge path 68a so that the air is discharged to the front end side of the rotation portion 75. Further, the journal portion 74 includes a second impact member side air discharge path 72Ab which is formed between the attachment portion 74a and the pipe 66 when they are fitted to each other and is formed in the periphery of the first impact member side air discharge path so as to be formed as a fan-shaped space between the cross-shaped portions communicating with the internal air discharge path A. By the second impact member side air discharge path 72Ab, the air is discharged from the internal air discharge path 68a to the discharge grooves 75a of the rotation portion 75.

The accumulation portion 76 includes a third impact member side air discharge path 72Ac which is formed at the center portion thereof, rotatably fixes the rotation portion 75 to the end portion side of the nozzle discharge opening 68 at the front end side of the shaft portion 74b of the journal portion 74, and communicate with the first impact member side air discharge path 72Aa. Thus, even when the water droplets of the mixture are accumulated in the front end side along the side surfaces 72Ad and 72Ae or the discharge grooves 75a through the collision with the tapered member 72A, the water droplets may be scattered to the outside by the rotation of the rotation portion 75. In this way, even in the gas-liquid mixing nozzle 60A according to the third embodiment, any problem concerned with the water droplets does not occur as in the case of the gas-liquid mixing nozzles 10 and 60.

(Examples of Environment Purification Liquid Spray System Using Gas-Liquid Mixing Nozzles According to First to Third Embodiments)

Figure 7A:
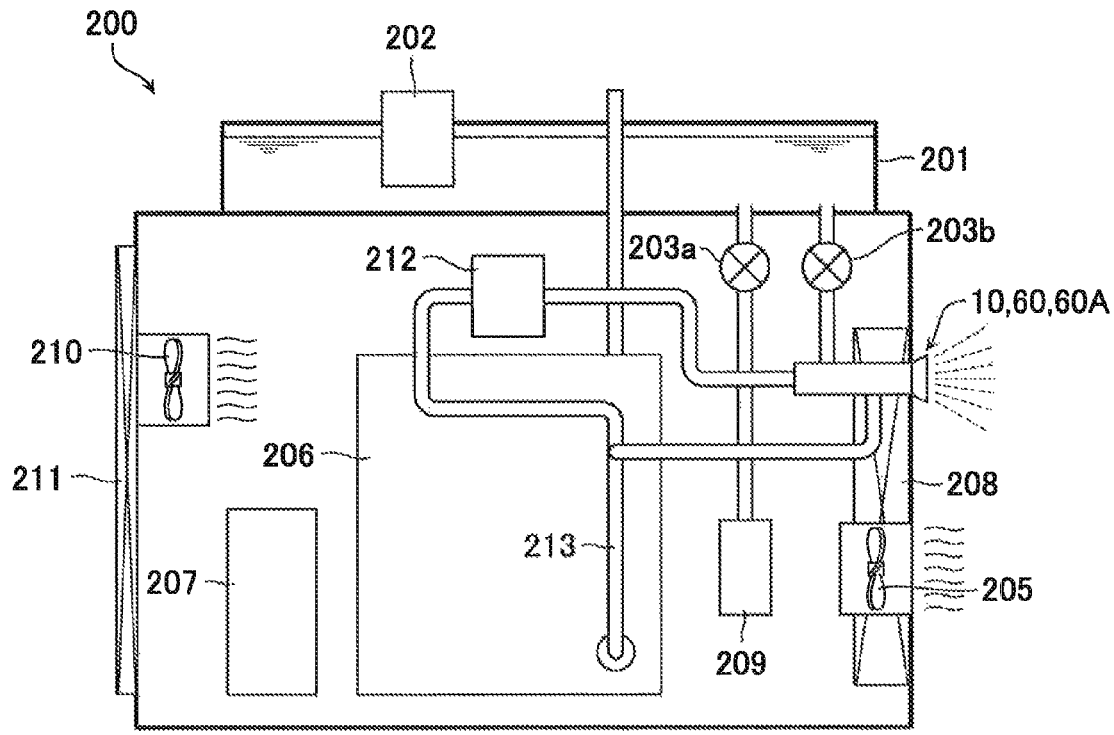
Figure 7B:
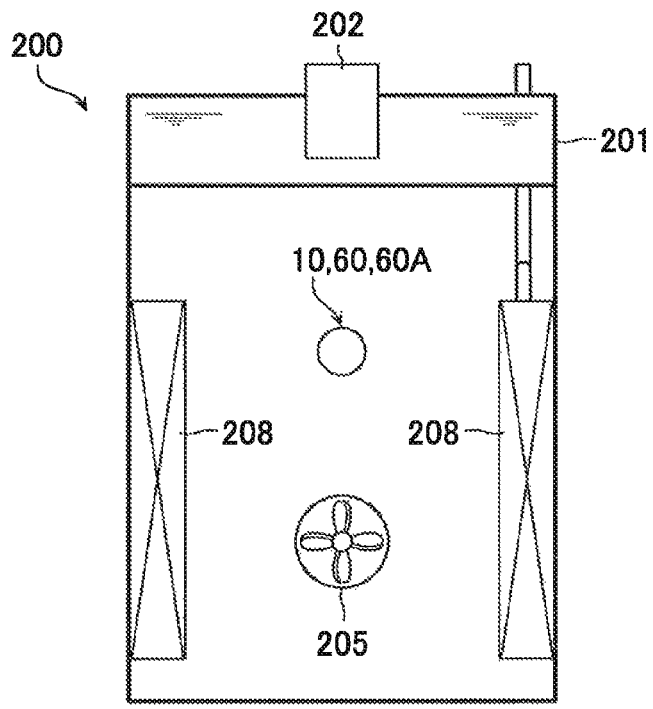

The gas-liquid mixing nozzles 10, 60, and 60A according to the first to third embodiments are used to efficiently produce and burn emulsion fuel. In addition, the gas-liquid mixing nozzles 10, 60, and 60A may be appropriately applied to an environment purification liquid spray system which supplies a liquid for environment purification to an environment purification liquid spray system. FIG. 7 is a diagram illustrating an example of the environment purification liquid spray device which is used in the environment purification liquid spray system, where in particular, FIG. 7A is a side view illustrating the configuration of the device and FIG. 7B is a front view illustrating the configuration of the device.

The gas-liquid mixing nozzles 10, 60, and 60A according to the first to third embodiments are used to mix three types of materials, the air, the fuel, and the water, but in the case of the application to the environment purification liquid spray system, the nozzles are used to mix the liquid and the air for the environment purification.

For example, when the configuration related to the fuel in the gas-liquid mixing nozzles 10, 60, and 60A is eliminated or the configuration related to the fuel is changed to the configuration of circulating and discharging the liquid for the environment purification, the nozzles may be applied to the environment purification liquid spray system. Then, even in the case where the gas-liquid mixing nozzles 10, 60, and 60A are applied to the environment purification liquid spray system, the operation and effect which is the same as that of the description above may be obtained and the environment purification material may be produced and sprayed in the optimal state.

Specifically, as illustrated in FIG. 7, an environment purification liquid spray device 200 which constitutes the environment purification liquid spray system includes a water tank 201 which stores water, a first mineral container 202 which is immersed into the water stored in the water tank 201 and supplies mineral constituents, an electromagnetic valve 203a which supplies a mineral solution from the water tank 201 to the second mineral container 209, and an electromagnetic valve 203b which supplies the mineral solution from the water tank 201 to the gas-liquid mixing nozzles 10, 60, and 60A.

Further, the environment purification liquid spray device 200 includes a fan 205 which discharges the mineral solution supplied to the second mineral container 209 into air and an air pump 206 which supplies air to the gas-liquid mixing nozzles 10, 60, and 60A in a pressurized state. Furthermore, the environment purification liquid spray device 200 includes a control device 207 which controls the entire environment purification liquid spray device 200 and controls the operations of the electromagnetic valves 203a and 203b or respective components, and an ultraviolet ray lamp 208 which irradiates an ultraviolet ray to the mist-like materials respectively discharged from the gas-liquid mixing nozzles 10, 60, and 60A and the fan 205.

Further, the environment purification liquid spray device 200 includes a fan 210 which introduces external air to the inside through a filter 211 and an ozone generation device 212 which applies ozone ($O_3$) to at least a part of the air supplied from the air pump 206 to the gas-liquid mixing nozzles 10, 60, and 60A. Furthermore, the respective components such as the gas-liquid mixing nozzles 10, 60, and 60A, the air pump 206, and the ozone generation device 212 are connected to each other by a pipe 213.

As the environment purification material accumulated in the first mineral container 202, charcoal, catechin, theanine, selfeel (trade name, manufactured by Nichirin Chemical Co., Ltd.), a leaf milky liquid of a mulberry, and the like may be exemplified. The charcoal is obtained by char-grilling (carbonizing) a tree or the like growing as a raw wood by absorbing nutrients from a ground together with moisture. The nutrients absorbed during the growing period include mineral constituents, magnesium (Mg), natrium (Na), germanium (Ge), kalium (K), calcium (Ca), zirconium (Zr), iron (Fe), manganese (Mn), silicon (Si), phosphorus (P), and the like. The catechin inactivates a virus by directly discharging a solution (eluate) into the air.

In the mineral constituents, the natrium and the kalium are alkali metal, and the calcium is earth metal, which is comparatively high in the content ratio and may be easily eluted into the water of the water tank 201. By the mineral constituents from the first mineral container 202, the water inside the water tank 201 becomes alkali solution and alkali ion water.

Furthermore, kalium, calcium, natrium, magnesium, and aluminum may be numbered in this order according to the ionization strength. The alkali solution which contains metal having a strong elution reaction with respect to water may be produced by immersing, for example, charcoal into water. That is, $H_2O$ as water is $H^+ + OH^- \Leftrightarrow H_2O$, in which it is generally known that a hydrogen ion coming out of acid and a hydroxide ion coming out of base (alkali) are linked to each other so that water of $H_2O$ is obtained, which may be understood as the neutralization of acid and base.

Then, since the mineral of alkali metal which is eluted from the charcoal into the water is base (alkali), it becomes a hydroxide ion $OH^-$. Since the environment purification liquid spray device 200 supplies a minus ion water obtained by the hydroxide ion $OH^-$ from the water tank 201 to the gas-liquid mixing nozzles 10, 60, and 60A so as to be sprayed into the air, the mist-like material which is the assembly of the fine water molecules has a characteristic of a minus ion.

In this way, when the environment purification material is mixed with the water and the result is sprayed, it is possible to satisfactorily obtain an insect killing effect or an organic material decomposition effect. Further, when the environment purification material finishes the decomposition, the environment purification material returns to the environment of water or oxygen, so that it becomes an environment friendly material.

Furthermore, the environment purification material may include, for example, a soluble fiber such as catechin or theanine of a green tea, and may further include a fruit of a neem eliminating destructive insects or eluted extract of a leaf thereof. When theses are mixed with the water inside the water tank 201 and are sprayed, it is possible to obtain an air cleaning effect which is not poisonous and harmful to a human body. Furthermore, nano particles of a pyrethrum have an insect killing effect, and when the nano particles are used, the environment purification liquid spray system including the environment purification liquid spray device 200 may be used as an insect killing system.

Further, when ozone is contained in the air supplied to the gas-liquid mixing nozzles 10, 60, and 60A by the ozone generation device 212 disposed adjacent to the air pump 206, the ozone and the water may be mixed with each other inside the nozzle. Here, in the related art in which the ozone is contained in the water, there has been problems that the content efficiency is extremely poor and the ozone disappears.

However, according to the gas-liquid mixing nozzles 10, 60, and 60A of the first to third embodiments, the water becomes a cluster-like mist so that it may be stably adsorbed to the ozone and may be carried for a long period of time. It is considered that this is caused by the effect that the cluster-like water is scattered by discharging air into the discharged water at a strong pressure and a minus ion is generated at that time, so that the ozone is stably adsorbed.

In this way, when the ozone is sprayed from the gas-liquid mixing nozzles 10, 60, and 60A together with the pressurized air, the ozone may be discharged into the air in a state where the ozone adheres to the mist-like particles of the minus ions.

Furthermore, the ultraviolet ray lamp 208 is configured to irradiate ultraviolet rays with two types of wavelengths, a wavelength of 184.9 nm and a wavelength of 253.7 nm.

Then, the environment purification liquid spray device 200 is configured to irradiate the ultraviolet ray to the flow of the minus ion water containing the ozone sprayed into the air from the gas-liquid mixing nozzles 10, 60, and 60A and the flow of the air containing the minus ion water sprayed into the air by the fan 205 by using the ultraviolet ray lamp 208.

Specifically, it is known that the ultraviolet ray with a wavelength of 184.9 nm dissociates a part of oxygen in the air into oxygen atoms so as to produce the ozone. Thus, when the ultraviolet ray which produces the ozone is irradiated by the ultraviolet ray lamp 208 and the ozone is discharged into the air along with the mist-like material of the minus ion water sprayed from the gas-liquid mixing nozzles 10, 60, and 60A, it is possible to produce hydroxyl radical (OH) in the air and kill virus cells through the oxidization.

The hydroxyl radical is produced by the reaction with the oxygen atom produced by the dissociation of the ozone since there are water molecules. Since the minerals such as kalium which is effectively used for the production of the hydroxyl radical is eluted into the solution inside the water tank 201, even when the concentration of the ozone is made to be safe within 0.1 ppm, the hydroxyl radical may be sufficiently produced. The mist-like material having a minus charge may be easily adhered and adsorbed to a material such as dirt or dust in the air, so that it may be adhered to a virus or the like in the air. Then, the hydroxyl radical is produced in the periphery of a cell wall of a virus or the like, and hence the cell wall may be broken.

The mist-like material which is formed by spraying the alkali ion water inside the water tank 201 using the gas-liquid mixing nozzles 10, 60, and 60A is a mist of a minus ion, and is adsorbed and adhered to the plus potential. For example, as the characteristics of the concentrated alkali of about pH 11, it has an insect killing or eliminating effect, so that the effect of oxidization power of the ozone or the hydroxyl radical having the stronger oxidization power may be obtained. Accordingly, the synergetic effect may be obtained.

Further, it is proved that the ultraviolet ray having large energy is absorbed into the cell of the virus, so that the nucleoprotein structure is changed and the cell is killed when the ultraviolet ray with a wavelength of 253.7 nm is irradiated to the mist-like material discharged by the fan 205 from the ultraviolet ray lamp 208. As the characteristics of the wavelength of the ultraviolet ray having such a sterilizing effect, the wavelength is almost the same according to the bacterial species, and the highest sterilizing effect is obtained in the wavelength of 250 nm to 260 nm. When such an ultraviolet ray is irradiated to the mist-like material of the minus ion water sprayed from the environment purification liquid spray device 200 and the result is discharged into the air, the high sterilizing effect may be obtained regardless of the day and the night.

Further, it is known that the kalium which is contained with a comparatively large content in the minus ion water inside the water tank 201 acts on the water molecules sprayed from the gas-liquid mixing nozzles 10, 60, and 60A so that hydroxyl radical and hydrogen peroxide are produced. Furthermore, hydroxyl radical is also produced by the reaction according to iron (Fe), manganese (Mn), or the like which is a transition element in the minus ion water.

In this way, according to the environment purification liquid spray system using the environment purification liquid spray device 200, it is possible to reliably obtain a sterilizing effect, an insect killing effect, an effect of purifying disease germ in the air, a deodorizing effect, and a freshness maintaining effect, which have been difficult to obtain in the related art, by spraying the environment purification material using the gas-liquid mixing nozzles 10, 60, and 60A according to the first to third embodiments and irradiating the ultraviolet ray from the ultraviolet ray lamp 208.

That is, according to the environment purification liquid spray device 200, a structure is realized which produces hydroxyl radical molecules dissociating and oxidizing toxic materials and having strong oxidization power through the natural mineral contained in a charcoal such as a wood coal or a bamboo coal using the gas-liquid mixing nozzles 10, 60, and 60A without increasing the content of the ozone. Further, when the pressurized solution (clean water such as tap water) having mineral constituents and compressed air are sprayed into the air and the solution is sprayed into the air together with the ozone containing air, a structure is realized which obtains a deodorizing effect, an insect killing effect, and a sterilizing effect.

Furthermore, when the air which is supplied to the gas-liquid mixing nozzles 10, 60, and 60A contains, for example, leaf powder of a mulberry, powder of a pyrethrum, leaf powder of a neem, and the like having a strong insect killing effect, it is possible to kill the insects without using a medical agent or kill the insects by spraying a solution having such powder constituents eluted thereto as a mist-like material. The solution having such constituents eluted thereto is not harmful to a human body.

Furthermore, as a method of eluting the mineral constituents to the water supplied to the gas-liquid mixing nozzles 10, 60, and 60A, for example, there is a method in which water is supplied from the water tank 201 into the first and second mineral containers 202 and 209 so as to obtain water having mineral constituents eluted thereto in addition to the above-described method. In addition, the environment purification liquid spray device 200 is configured to sufficiently obtain the above-described sterilization and insect killing effect even when the gas-liquid mixture type nozzle applied in the past is used instead of the gas-liquid mixing nozzles 10, 60, and 60A.

Furthermore, the content of the ozone, the wavelength of the ultraviolet ray, the mist-like material spray condition, or the like is not limited to the above-described example, and may be arbitrarily set depending on the use environment or the use purpose. Furthermore, when a perfume is mixed into water in advance by using the production of minus ions, it is possible to highly obtain both a comfort effect and a deodorizing effect using the perfume.

While the most preferable embodiments of the invention have been described, the technical scope of the present invention is not limited to the scope of the respective embodiments. In the respective embodiments, various modifications or improvements may be made.

For example, in the gas-liquid mixing nozzles 10, 60, and 60A, the water may be replaced by the ozone-nano bubble water. When the ozone-nano bubble water is used, the oxidization and combustion effect of carbon, magnesium, or the like to be mixed is promoted. This presents an effect that the fuel used in the past is reduced with an increase in the mixture ratio of the atoms and molecules having strong combustion and explosive power such as carbon or magnesium with respect to the water.

Further, in the gas-liquid mixing nozzles 10, 60, and 60A applied to the environment purification liquid spray device 200, since the ozone-nano bubble water is used as the sprayed water, the sterilizing effect may be exhibited. The micro bubbles disappear under water, but the nano bubbles sustain and have a sterilizing effect several times larger than chlorine.

By using such ozone-nano bubble water, it is possible to obtain the sterilizing effect, the insect killing effect, the disinfecting effect, the deodorizing effect, and the like in many fields.

According to the description of claims, it is apparent that the embodiments which are modified or improved as described above are included in the tehnical scope of the present invention.

DESCRIPTION OF REFERENCE NUMERALS

10, 60, 60A Gas-liquid mixing nozzle
11, 61 Front member
12, 62 Intermediate member
12*e*, 63*a* Water nozzle coupling
13, 63 Rear member
13*d*, 67 Fuel nozzle coupling
14, 64 Rear air coupling
21, 73 Front air coupling
22, 72, 72A Impact member
200 Environment purification liquid spray device
201 Water tank
202 First mineral container
205 Fan
206 Air pump
207 Control device
208 Ultraviolet ray lamp
209 Second mineral container
210 Fan
211 Filter
212 Ozone generation device

The invention claimed is:

1. A gas-liquid mixing nozzle comprising:
   an internal air discharge path which discharges air toward a center portion of a nozzle discharge opening;
   an external air discharge path which discharges air from the outer edge portion of the nozzle discharge opening;
   at least one liquid introduction path which is disposed between the internal air discharge path and the external air discharge path and introduces liquid into the nozzle discharge opening, the liquid introduction path comprising a water introduction path for introducing water as one main component of the liquid and a fuel introduction path for introducing fuel as another main component of the liquid; and
   an impact member with which a mixture of the air and the liquid mixed with each other in outlets of the internal air discharge path and the liquid introduction path collides so that the mixture of the air and the liquid becomes mist with finer particles,
   the external air discharge path discharging a mixture of the air and the mist from the nozzle discharge opening, and
   the impact member including a penetration hole formed along a center axis of the impact member extending from the rear end portion of the impact member to the front end portion of the impact member, the rear end of the penetration hole communicating with an internal space of the internal air discharge path.

2. A gas-liquid mixing nozzle comprising:
   an internal air discharge path which discharges air toward a center portion of a nozzle discharge opening;
   an external air discharge path which discharges air from the outer edge portion of the nozzle discharge opening;
   at least one liquid introduction path which is disposed between the internal air discharge path and the external air discharge path and introduces liquid into the nozzle discharge opening, the liquid introduction path comprising a water introduction path for introducing water as one main component of the liquid and a fuel introduction path for introducing fuel as another main component of the liquid; and an impact member with which a mixture of the air and the liquid mixed with each other in outlets of the internal air discharge path and the liquid introduction path collides so that the mixture of the air and the liquid becomes mist with finer particles, the external air discharge path discharging a mixture of the air and the mist from the nozzle discharge opening, and the impact member rotating about the central axis of a nozzle by the force of wind of the mixture of the air and the liquid and including a penetration hole formed along a center axis of the impact member extending from the rear end portion of the impact member to the front end portion of the impact member, the rear end of the penetration hole communicating with an internal space of the internal air discharge path.

\* \* \* \* \*